(12) United States Patent
Ammann

(10) Patent No.: US 8,709,014 B2
(45) Date of Patent: Apr. 29, 2014

(54) DEVICE, KIT, AND A METHOD FOR HANDLING A MEDICAL IMPLANT

(75) Inventor: Oliver Ammann, Burgdorf (CH)

(73) Assignee: Stryker Trauma GmbH (DE)

( * ) Notice: Subject to any disclaimer, the term of this patent is extended or adjusted under 35 U.S.C. 154(b) by 1870 days.

(21) Appl. No.: 11/586,238

(22) Filed: Oct. 25, 2006

(65) Prior Publication Data

US 2008/0015632 A1   Jan. 17, 2008

(30) Foreign Application Priority Data

Jul. 14, 2006 (EP) ................................. 06014724

(51) Int. Cl.
  *A61B 17/58* (2006.01)
  *A61B 17/80* (2006.01)

(52) U.S. Cl.
  USPC .......................................... 606/86 B; 606/71

(58) Field of Classification Search
  USPC ................... 606/70–71, 86 B, 96, 104, 205, 606/280–299, 300–330, 902–906, 86 R, 606/86 A, 99
  See application file for complete search history.

(56) References Cited

U.S. PATENT DOCUMENTS

| | | | | |
|---|---|---|---|---|
| 2,406,952 A | * | 9/1946 | Josepho | 81/452 |
| 4,877,020 A | * | 10/1989 | Vich | 606/86 R |
| 5,885,299 A | * | 3/1999 | Winslow et al. | 606/99 |
| 5,897,555 A | * | 4/1999 | Clyburn et al. | 606/54 |
| 6,299,616 B1 | * | 10/2001 | Beger | 606/86 R |
| 7,207,995 B1 | * | 4/2007 | Vandewalle | 606/104 |
| 7,648,508 B2 | * | 1/2010 | Lutz et al. | 606/86 R |
| 2002/0045898 A1 | | 4/2002 | Freid et al. | |
| 2002/0099378 A1 | | 7/2002 | Michelson | |
| 2002/0169453 A1 | * | 11/2002 | Berger | 606/73 |
| 2003/0125750 A1 | * | 7/2003 | Zwirnmann et al. | 606/104 |
| 2003/0153921 A1 | * | 8/2003 | Stewart et al. | 606/72 |
| 2004/0127896 A1 | * | 7/2004 | Lombardo et al. | 606/61 |
| 2004/0254579 A1 | * | 12/2004 | Buhren et al. | 606/71 |
| 2004/0260291 A1 | * | 12/2004 | Jensen | 606/69 |
| 2005/0070918 A1 | * | 3/2005 | Zwirnmann et al. | 606/104 |
| 2005/0071013 A1 | * | 3/2005 | Zubok et al. | 623/17.16 |
| 2006/0116679 A1 | * | 6/2006 | Lutz et al. | 606/69 |
| 2006/0116680 A1 | * | 6/2006 | Kugler et al. | 606/69 |
| 2006/0116686 A1 | | 6/2006 | Crozet | |
| 2006/0116689 A1 | | 6/2006 | Albans et al. | |

FOREIGN PATENT DOCUMENTS

EP  1661525  5/2006

* cited by examiner

*Primary Examiner* — Nicholas Woodall
*Assistant Examiner* — Larry E Waggle, Jr.
(74) *Attorney, Agent, or Firm* — Lerner, David, Littenberg, Krumholz & Mentlik, LLP

(57) ABSTRACT

A medical device for handling an implant, the medical device comprising a loading section adapted to be loaded with an insert element to be inserted into a hole formed in an implant, and a guiding section adapted to be guided by a pin inserted into the hole formed in the implant for guidedly inserting the insert element into the hole formed in the implant.

29 Claims, 13 Drawing Sheets

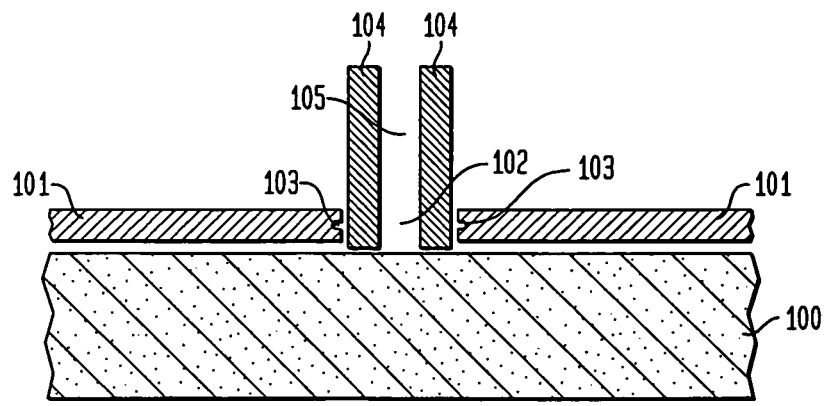
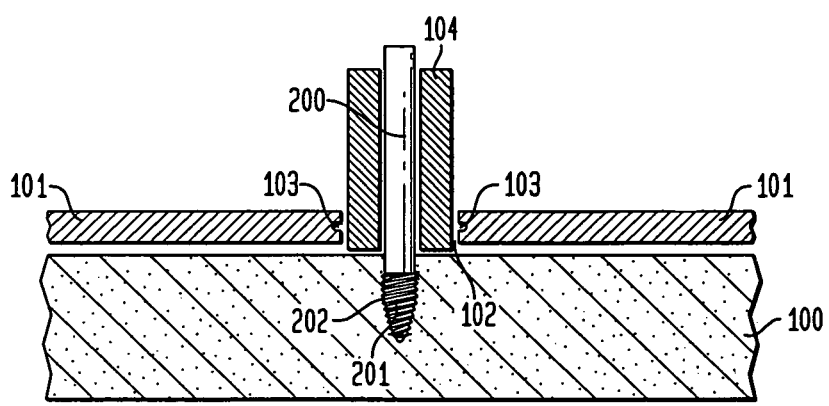
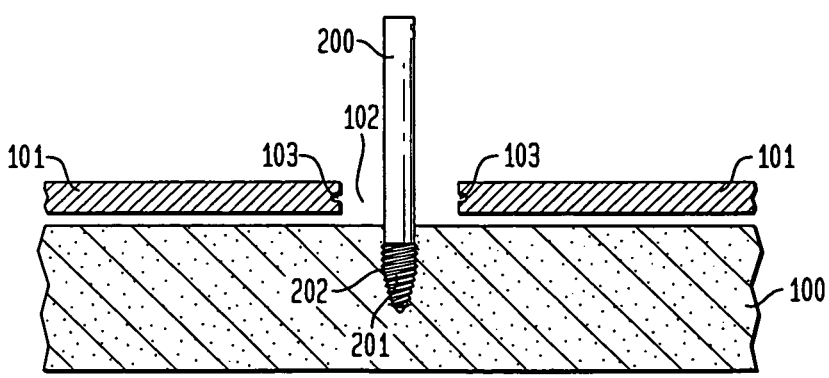

DEVICE, KIT, AND A METHOD FOR HANDLING A MEDICAL IMPLANT

BACKGROUND OF THE INVENTION

The invention relates to a medical device for handling an implant and a method of handling an implant.

The invention further relates to a medical kit for handling an implant.

Bone plates may be fixed at a bone using nails or screws in order to stabilize a fracture.

US Publication 2006/0116686 discloses a screw fastener for attachment to an orthopedic component such as an orthopedic plate for use in connection with fracture fixation, joint reconstruction or spinal stabilization or fusion as having a shank with at least two different shank diameters, one in a plate engaging portion of the shank and one in the bone or other component engaging portion of the shank. At least two of the different shank diameters on the shank include threads, the threads on the two different diameter portions each having substantially the same thread height and pitch. A plate having a threaded aperture, or an adapter having a threaded aperture, is sized such that the threads of the smaller diameter shank portion engage and cooperate with the internal threads of the aperture to correctly align the screw fastener and the implant as the screw fastener is threaded through the implant. The threads on the larger diameter shank portion and the internal threads of the aperture of the implant are sized so that the threads of the larger diameter shank portion are fully engaged with the internal threads of the orthopedic implant.

U.S. Publication 2004/0254579 discloses an implantable orthopedic device having a load-bearing element, such as a bone plate, with at least one opening for a fixation element and one insert which can be inserted in an inclined opening in a receptacle in the bore. This insert has an external form that is at least partially complementary to the internal form of the receptacle and a central through-bore for receiving the body of the fixation element such as a bone screw. The insert also provides a locking system for holding the insert in the receptacle, in which the insert exhibits at least one locking mechanism with which conformal locking with the load-bearing element may be achieved.

U.S. Publication 2006/0116680 discloses an extractor device to extract an insert to be used with a bone connection element such as a bone plate having at least one opening for a bone screw used with said insert. The extractor device has an outer hollow sleeve having proximal abutment surface being able to engage a surface portion of the bone connection element, and an inner bar having a diameter enabling the insertion of the bar into the hollow sleeve. The bar has a threaded leading end to engage the thread of the insert to be extracted. The hollow sleeve has an inner thread and the inner bar has an outer threaded element for engaging the inner thread of the hollow sleeve. The outer threaded element is positioned with respect to the bar in a longitudinal position to enable the thread at its leading end to extend beyond the proximal abutment surface of the sleeve to be threaded into the insert.

However, there is still a need for an efficient handling of an implant.

SUMMARY OF THE INVENTION

According to exemplary embodiments of the invention, there are provided a medical device for handling an implant, a medical kit for handling an implant, and a method of handling an implant.

According to an exemplary embodiment of the invention, a medical device for handling an implant is provided, the medical device comprising a loading section adapted to be loaded with an insert element to be inserted into a hole formed in an implant, and a guiding section adapted to be guided by a pin inserted into the hole formed in the implant for guidedly inserting the insert element into the hole formed in the implant.

According to another exemplary embodiment of the invention, a medical kit for handling an implant is provided, the medical kit comprising a medical device having the above mentioned features.

According to still another exemplary embodiment of the invention, a method of handling an implant is provided, the method comprising loading a loading section of a medical device with an insert element to be inserted into a hole formed in an implant, and guiding a guiding section of the medical device by a pin inserted into the hole formed in the implant for guidedly inserting the insert element into the hole formed in the implant.

In the context of this application, the term "medical device" may particularly denote any apparatus being suitable (for instance with regard to biocompatibility, sterilization, etc.) for applications related to the health system, like surgery. Particularly such "medical devices" may be appropriate for use by physicians, nurses, etc.

The term "handling" may particularly denote any manual operation of the medical device by a user, for instance before, during or after surgery.

The term "implant" may particularly denote any physical structure which is foreseen or designed to be introduced into or attached to a body of a physiological object, like a human being or an animal. Examples for implants are bone plates adapted to be connected to a bone, or bone screws adapted to be screwed into a bone.

The term "insert element" may particularly denote any component being shaped and dimensioned to be securely inserted in a target structure. More particularly, an insert element may be an adapter piece to be inserted into a hole of a bone plate to thereby equip an unthreaded hole with a thread foreseen in the insert element. Thus, inserting an insert element into the target structure may selectively adjust the functional properties of the target structure by help of the insert element.

The term "loading" may particularly denote detachably equipping a loading section of the medical device with an insert element for a selective deposition of the insert element at a target apparatus.

The term "guidedly inserting" may particularly denote inserting the insert element into a hole of the implant under control of a mechanical guiding mechanism to thereby allow accurate spatial positioning (in longitudinal and/or in angular manner) of the insert element into the hole of the implant.

The term "forceps" may particularly denote a mechanism having two leg elements (or branches) which are mounted (for instance angularly to one another) for an anatomically suitable actuation by a hand of an operator. When actuating a forceps mechanism, the spatial relationship of the leg elements (or branches) may be selectively altered, thereby mechanically acting precisely on a portion to be handled by the forceps, particularly making use of a lever action.

The term "kit" may particularly denote a set comprising multiple components adapted for cooperative use. For instance, such a kit may be a modular construction set including individual or separate components for functional interaction. The term "kit" may particularly denote an arrangement of a plurality of individual or separate components which may be used independently from one another but which form together a medical system.

The medical kit may comprise the insert element, for instance an insert element having one or a plurality of the above-mentioned properties.

According to an exemplary embodiment, a medical device is provided which allows to assist an operator in inserting an insert element/locking insert into a hole of an implant, for instance of a bone plate, by simply guiding the medical device along a guiding pin which has been previously inserted into the hole. When a tip of the medical device loaded with the insert element has reached the hole of the bone plate, the medical device may snap on the pin. Applying a pressure on the medical device may then promote insertion of the insert element into the hole. Actuating a button of the medical device may then release the medical device from the pin and may allow a removal of the medical device from the implant with the fixed insert element, and subsequent a removal of the pin.

A mechanism may thus be provided allowing to click or snap an outer surface of the insert element into a corresponding recess of the bone plate. Such an insert element may comprise an inner thread so as to allow a user to convert an unthreaded hole in a bone plate into a threaded hole using the insert element as an adapter. By taking these measures, such an inner thread may be formed indirectly in the bone plate making use of the insert element, for instance for screwing a bone screw into the threaded insert element inserted in the bone plate and into the bone.

According to an exemplary embodiment, an angularly stable plate or implant having oblong holes and threaded holes may be selectively manipulated so as to be brought in accordance with a configuration which is desired for a specific application, for instance a surgical operation for treating a fracture of a bone. With such a method of inserting the insert element into an oblong hole with only a small pressure acting on the implant and on the bone, this oblong hole may be functionally converted or adjusted to provide a threaded hole. Such a mechanism may be realized using a forceps for pressing the insert element into the oblong hole, wherein the forceps may be guided by a guiding pin.

According to an exemplary embodiment, a locking inserter may be provided which may be used before or during a medical operation, since an essentially forceless insertion of the locking insert is enabled also during an operation, that is in a state in which the implant is already mounted on or in a body of an object under examination (like a human or animal patient). Therefore, according to an exemplary embodiment, a minimal invasive method may be provided to insert such an (for instance threaded) insert element into an implant which may already be located at or in a body.

According to an exemplary embodiment, a bone plate or any other implant may be attached to a bone (for instance a broken bone). Then, a pin sleeve may be attached to a hole formed in the bone plate. Through such a pin sleeve, a pin may be guided through the hole of the implant which pin can be screwed into the bone using an appropriate power tool. Such a pin may have a self-tapping and self drilling thread, so as to be able to be threaded inside the bone with low effort. When the pin is fixed in the bone as a mechanical guiding structure, the pin sleeve may be removed from the arrangement, in which the pin has already been screwed into the bone.

For continuing the spatially controlled insert element insertion procedure, the locking insert may be loaded or mounted on the forceps. The forceps may then be shifted over the pin so that the pin is received in an inner bore of the forceps, thereby allowing the inner bore and the pin to be cooperatively guided. The locking insert provided on a tip of the forceps may have a hole through which the pin may be guided when the pin is guided through the forceps. In other words, the pin and the forceps may be guided with respect to one another by guiding the pin through the guiding section of the forceps. It is also possible that the pin inserted in such a guide section of the forceps is fastened in the forceps at a particular position, to enable stability with regard to a longitudinal position and with regard to an angular position. When the forceps has been guided towards the oblong hole of the implant, the forceps may be fixed to the pin by snapping. Then, pressing on an actuation section of the forceps may allow the loaded insert element (optionally supported by a force, like a spring force) to be pressed into the implant, for instance into an oblong hole of a bone plate. The forceps may then be disassembled from the arrangement, that is to say may be removed from the bone plate. For this purpose, a button or any other actuation mechanism may be actuated so as to release the forceps from the pin to allow the removal of the forceps. Then, the pin may be screwed out of the bone. What remains is the bone plate having the insert element pressed therein, and a hole preformed in the bone by the pin. Then, a bone screw may be screwed in the bone making use of the thread of the insert element and of the pre-formed hole in the bone. Such a bone screw may then be forced to extend into the bone, particularly into the hole which has previously been formed by the pin. Therefore, a separate bore procedure may be avoided. In order to use the hole defined by the pin, the outer diameter of the pin may be adjusted to a core or root diameter of the bone screw.

Therefore, according to an exemplary embodiment, a locking insert forceps may be provided. To obtain axially stable fixation in the diaphyseal region of long bones with a locking plate system, a locking insert may be used. With a locking insert mechanism according to an exemplary embodiment of the invention, it may be made possible to insert the locking insert intra operatively. Conventionally, it may be necessary to press the locking insert into the implant on the back table before implanting the plate. Because it may be desired by a surgeon to insert the locking insert intraoperatively and minimally invasive, the locking insert forceps according to an exemplary embodiment of the invention may be used.

Therefore, a device is provided that allows a minimal invasive insertion of locking inserts intra operatively. It is possible to apply essentially no or only a small force to the fracture during this procedure, thereby preventing a loss of reduction.

According to an exemplary embodiment, a centering pin with a threaded tip may be screwed through a guide for the centering pin into the bone. The guide for the centering pin may fit into a hole in the plate which may be compatible with the locking insert. With the guide for the centering pin, it may be ensured that the centering pin has the correct angle and position.

After setting the centering pin, the locking insert forceps holding the insert element may be inserted over the centering pin. The forceps may snap into the grooves of the centering pin. With this connection, the counter force (or counter poise) for pressing the locking insert in the plate may be generated.

The medical device may comprise a guiding section which may be adapted to guide a pin, inserted into the hole formed in the implant. Such a guiding section may be a hollow tube in an interior of the medical device which may be sized to be able to receive the pin. By taking this measure, a proper geometrical arrangement between medical device and pin may be ensured or adjusted. This may allow to accurately define position and angular property of the system.

Such solutions may be advantageous over a conventional approach. According to such a conventional approach, to insert the locking inserts into implants, a locking insert inserter is used. In such a conventional approach, a locking insert is screwed on the inserter and is pressed into the implant on the back table. However, exemplary embodiments of the invention may be advantageous compared to such a solution, since the force acting on the (fractured) bone may be significantly reduced or even essentially eliminated.

Next, further exemplary embodiments of the medical device will be explained. However, these embodiments also apply for the medical kit and for the method.

The device may comprise an actuating section adapted to be actuated by a user for triggering insertion of the insert element into the hole formed in the implant. Such an optional actuating mechanism may be actuated by a hand of a user operating the device, allowing the release of the loaded insert element from the medical device and connecting it to the implant.

The loading section may comprise a spring element biased for holding the insert element. For instance, a flat spring or leaf spring or any other resilient mechanism (like a hollow cylindrical rubber element) may be used to detachably hold the insert element.

The loading section may be adapted to hold the insert element along at least a part (particularly along the entirety) of a circumference or perimeter thereof. For instance, the insert element may have an essentially circular outer circumference, wherein the loading section may surround this circumference partially or entirely.

The loading section may be adapted to releasably hold the insert element. In other words, the insert element can be loaded onto the loading section in a reversible manner. By actuating an actuation mechanism or by simply pressing on a component of the medical device attached to the hole in the implant, the loaded insert element may be removed from the loading section, for instance may be pressed into a hole of an implant.

Such an actuating section may comprise a button, a switch, and/or an actuable grip. For example, a surgeon or any other user may press a button for triggering insertion of the insert element into the hole of the implant or may simply pressing the loaded insert element into the hole of the implant. Alternatively, a switch may be operated to enable insertion of the insert element into the hole. Another possibility is the usage of a hand grip as used in forceps or scissors, wherein approaching the legs of the grip may initiate insertion of the insert element into the hole. Such a lever mechanism may allow operating the medical device with low force.

The guiding section may comprise a fastening mechanism adapted for detachably fastening the guiding section to the pin. Such a fastening mechanism may be a snap-fit connection, an engagement connection, a press-fit connection, a positive locking connection or a force closure connection. Using such a fastening mechanism which may be operated by a user, the pin inserted into the guiding section may be spatially fixed so as to ensure a proper arrangement or alignment between medical device and pin.

The fastening mechanism may be actuable by an, actuable button, an actuable switch, and/or an actuable grip.

The medical device may particularly be adapted as a forceps. The term "forceps" may, particularly denote an arrangement in which two legs of a hand grip may be held by the hand of a user. When one or both legs are operated manually, the function of the medical device may be carried out, for instance insertion the locking insert into a bone plate and/or decoupling of the guiding section from the pin.

In the following, further exemplary embodiments of the medical kit will be explained. However, these embodiments also apply to the medical device and to the method.

Apart from the medical device (a forceps, according to an exemplary embodiment), the medical kit may comprise the insert element which may be adjusted to the medical device (for instance with regard to dimensions, shapes, etc.).

Particularly, the insert element may comprise a structure or a body having a through hole which may be penetrated by the pin and by a bone screw. Such an insert element may comprise an inner thread formed at a, wall delimiting the through hole. Therefore, the insert element may have an essentially nut-shaped configuration and may serve to provide an inner thread for providing a screw connection between the insert element comprising implant and a bone screw.

The through hole may be adapted to be penetrated by a guiding pin to be inserted into the hole formed in the implant. In a scenario in which the insert element is loaded at the medical device (for instance a forceps) and the guiding pin is inserted through the hole of the bone plate into the bone of the patient, the guiding pin may be guided through the through hole of the insert element and through the guiding section of the medical device. This allows a proper alignment of the individual components of the medical system to be ensured.

The insert element may comprise a fastening element adapted to be fastened to a correspondingly designed further fastening element formed in the hole of the implant. The fastening element and the further fastening element may be adapted to provide a snap-fit connection, an engagement connection, a press-fit connection, a positive locking connection, or a force closure connection. In other words, the insert element and the implant may be matched to one another so that inserting the insert element into the hole of the implant may automatically generate a stable and fixed connection between insert element and implant.

The medical kit may comprise the implant having one or a plurality of the above-mentioned properties. Such an implant may be, for instance, a bone plate.

Such an implant may comprise the hole formed in a plate-like substrate and may comprise one or more further holes formed in the substrate. The hole may be unthreaded, and at least one of the further holes may have an inner thread. Therefore, the implant may be a bone plate with threaded and unthreaded holes, wherein insertion of an insert element into one of the unthreaded holes may convert this unthreaded hole into a threaded hole. This may allow increased flexibility for a user, for instance to generate further threaded holes in a bone plate. At least a part of the unthreaded holes may be oblong, thereby allowing positional adjustment of the insert element within the oblong hole.

The medical kit may comprise the pin adapted to be inserted through the hole formed in the implant into a bone.

Such a pin may have a threaded end portion, which may be self-tapping and self-drilling. Therefore, the end portion of the pin which may be shaped as a long rod may be directly screwed (using a conventional power tool) into a bone, without the need to pre-bore the bone. The pin may then have the function to provide a bore in which later a bone screw may be inserted, and to simultaneously provide a mechanical guiding for the forceps or medical device.

The pin may be adapted to be guidable through the insert element and through the guiding section of the medical device. This may allow the medical device to be mechanically guided by the pin, thereby increasing the accuracy of positioning individual components with respect to one another.

A pin insertion sleeve may be provided as a separate tool which may be removably attached to the hole formed in the implant and which may comprise a guiding bore through which the pin is guidable to thereby guide the pin through the hole formed in the implant. Such a pin insertion sleeve may be an auxiliary tool which may ensure the proper positioning of the pin within the hole of the implant protruding into the bone.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

BRIEF DESCRIPTION OF THE DRAWINGS

FIG. 1 to FIG. 6 show a cross-sectional view of a bone engaged by different components of a medical kit comprising a medical device according to an exemplary embodiment of the invention in different operation states while carrying out a method of handling an implant according to an exemplary embodiment of the invention;

DETAILED DESCRIPTION

Figure 4:
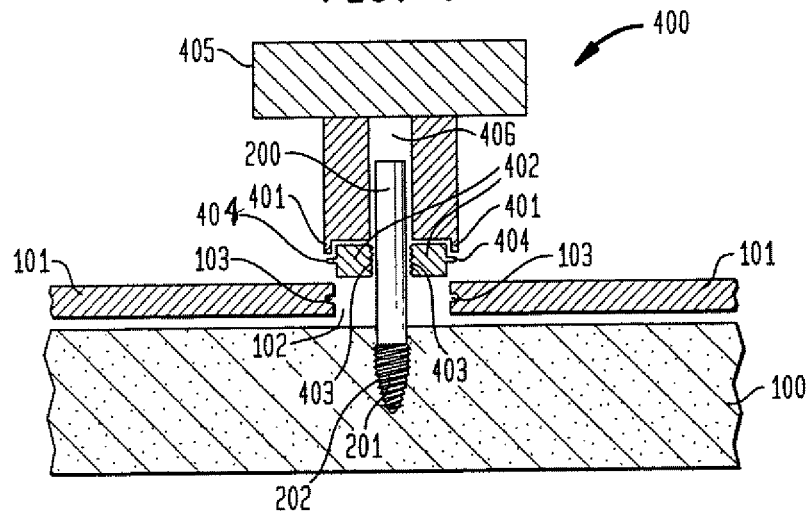

Referring to FIG. 1 to FIG. 6, there is shown schematically a medical system according to an exemplary embodiment of the invention will be explained in different operation states. The illustrations of FIG. 1 to FIG. 6 are cross-sectional views.

FIG. 1 shows a bone 100 being an object of a surgery. A bone plate 101 is positioned on the bone 100 or is connected to the bone 100, for example via one or more bone screws (not shown). The bone plate 101 has a non-threaded hole 102 and a further threaded hole 109 (see FIG. 10). Furthermore, grooves 103 are formed in a circumferential manner at an inner wall of the bone plate 101. These grooves are adapted to engage into protrusions formed at lateral walls of an insert element (see reference numeral 404 in FIG. 4) as will be described in the following in more detail.

In the operation state shown in FIG. 1, a pin sleeve 104 having an essentially hollow cylindrical shape is mounted on a surface of the bone 100 and extends through the hole 102 formed in the bone plate 101. The pin sleeve 104 is shaped and dimensioned to snugly fit in the hole 102.

As can be seen in FIG. 2, a pin 200 is inserted through a guide channel 105 of the pin sleeve 104, thereby allowing to properly define a position at which the pin 200 is screwed in the bone 100 by a power tool (not shown). The pin 200 has a tapered end portion 201 having a surface which comprises a self-tapping and self-drilling thread 202.

FIG. 3 shows the arrangement in an operation state in which the pin sleeve 204 has been removed. Therefore, the pin 200 remains fixedly screwed into the bone 100 at a proper position and with a proper angular orientation. In the following, the pin 200 may serve as a spatially well-defined reference structure.

FIG. 4 shows the arrangement in an operation state in which a medical device 400 such as the end of the forceps has been mounted on the arrangement shown in FIG. 3.

The medical device 400 comprises a loading section 401 shaped as a resilient spring mechanism 401A adapted for holding an essentially hollow cylindrical nut-shaped insert element 402 by the compression force of the spring. The insert element 402 has an essentially hollow cylindrical shape with an inner thread 403 and with protrusions 404 which are shaped and dimensioned to match to the grooves 103 of the bone plate 101. The spring for gripping the insert element 402 may be formed by slits 401B in the end of the loading section 401 (barrel) of the forceps 400.

According to an exemplary embodiment, the insert element 402 may be a clock-lock insert element, for instance an element as disclosed in US 2004/0254579 the disclosure of which is hereby incorporated by reference in the disclosure of this application, particularly with regard to the insert elements disclosed in US 2004/0254579.

An actuating section 405 which is only shown schematically in FIG. 4 allows a user to hold the medical device 400, to control operation of the medical device 400, and to trigger insertion of the insert element 402 from the loading section 401 into the hole 102, thereby bringing the protrusions 404 and the grooves 103 in engagement to one another to provide a stable fixation of the insert element 402 in the bone plate 101.

A guiding section 406 of the medical device 400 is provided as a tubular member adapted to be guided by the pin 200 inserted into the hole 102 formed in the bone plate 101. Thus, the guiding section 406 may be slid along the fixed pin 200, thereby guaranteeing a proper alignment of the medical device 400 holding the insert element 402.

Although not shown in FIG. 4, the medical device 400 may comprise a mechanism for fixedly holding the pin 200 in the guiding section 406. In other words, the pin 200 may be locked on the medical device 400 in an operation state in which the pin 200 is received in the guiding section 406.

When the insert element 402 comprising end portion of the medical device 400 is located close to the surface of the bone 100 in the hole 102, pressing the medical device 400 in forward direction may force the insert element 402 to be clicked in the hole 102.

In case that the pin 200 has been locked to the medical device 400, it may be released after having installed or assembled the insert element 402 in the hole 102.

Figure 5:
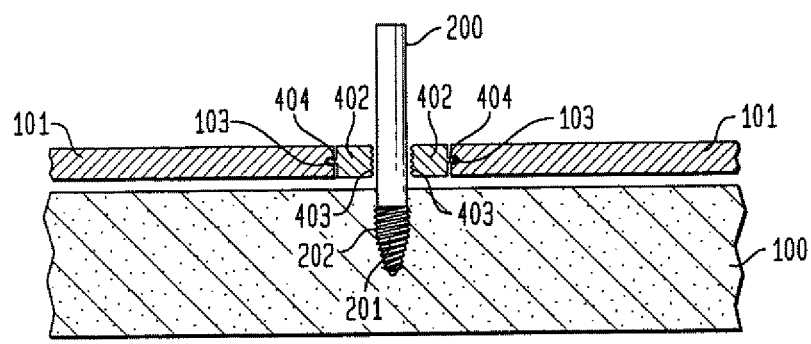

FIG. 5 shows the arrangement in an operation state after having clicked the insert element 402 into the hole 102 of the bone plate 101.

Subsequently, the medical device 400 may be removed. What remains, as shown in FIG. 5, is the insert element 402 being snugly inserted into the hole 102 of the bone plate 101, thereby providing a user-defined inner thread in the hole 102.

Figure 6:
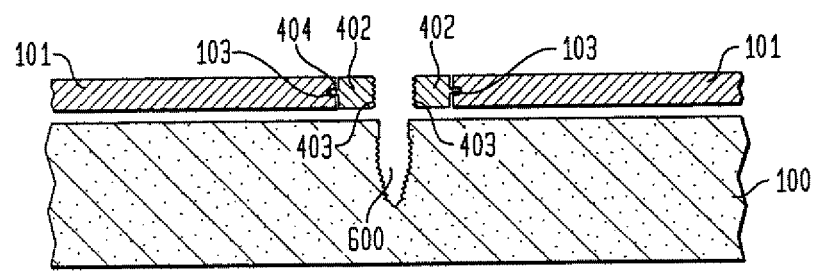

In FIG. 6, the pin 200 has been removed from the bone 100 by screwing, thereby generating a hollow bore 600 in the bone 100. In this bore 600, a bone screw may be screwed using the thread 403 of the insert element 402.

Figure 7:
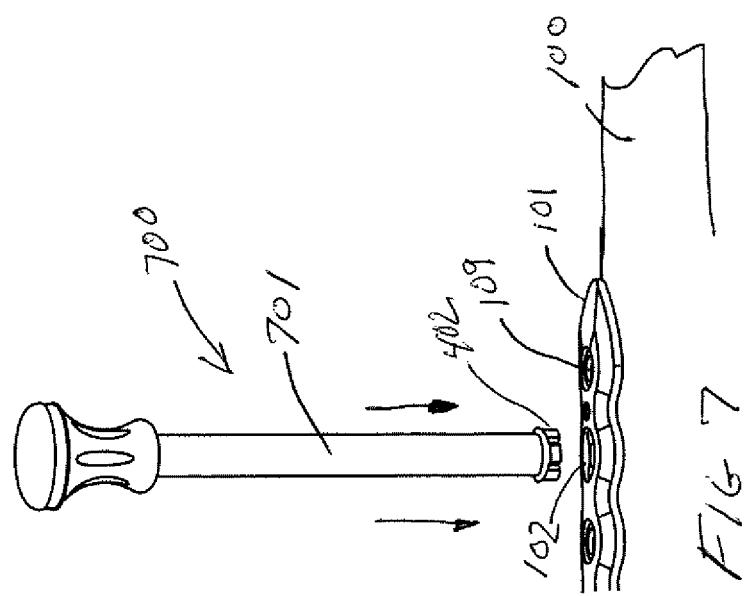
FIG. 7 illustrates a conventional mechanism for inserting a locking insert into a bone plate.

FIG. 7 illustrates a functional principle of a locking inserter 700 as conventionally used for inserting a locking insert 402 into a bone plate 101.

According to a conventional procedure, a locking insert 402 is threaded on the inserter 701. The locking insert 402 is pressed into the plate 101 (freehand without guiding). The locking inserter 701 is then removed.

In the following, referring to FIG. 8 to FIG. 13A, a functional principle of a locking insert forceps according to an exemplary embodiment of the invention will be explained.

Figure 8:
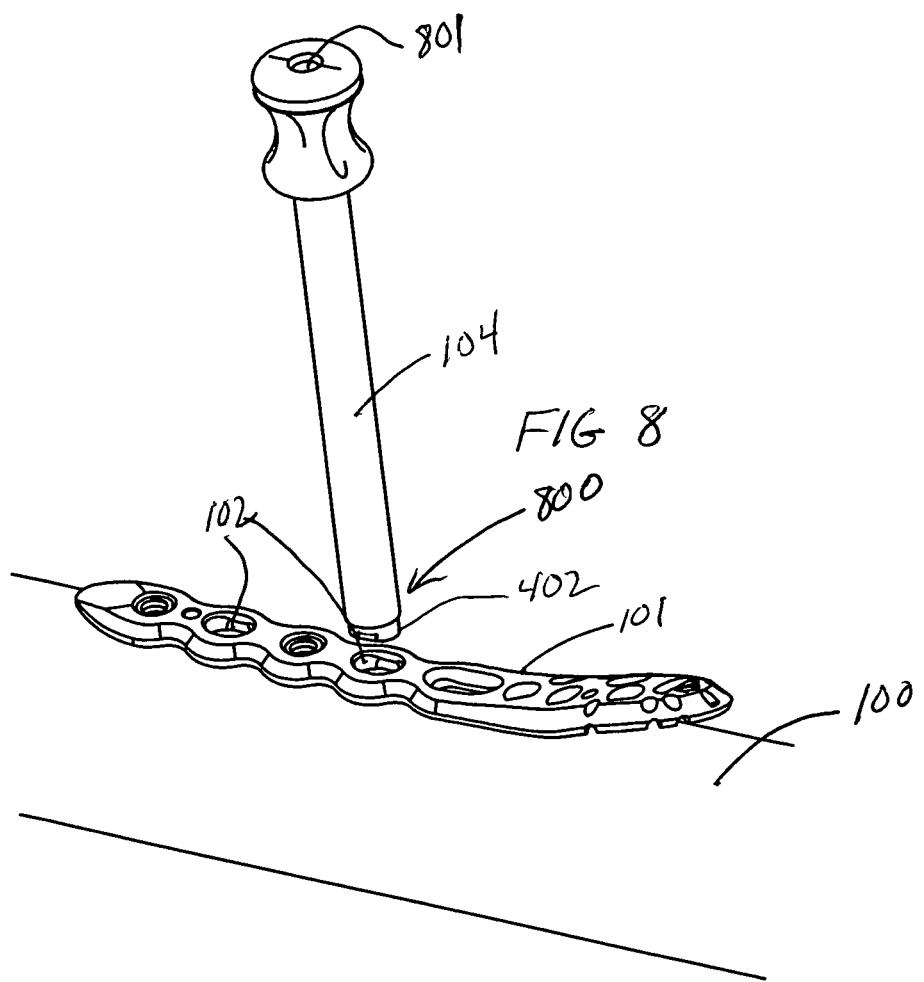
FIG. 8 to FIG. 13A illustrate a functional principle of a locking insert forceps using the conventional mechanism according to an exemplary embodiment of the invention.
Figure 9:
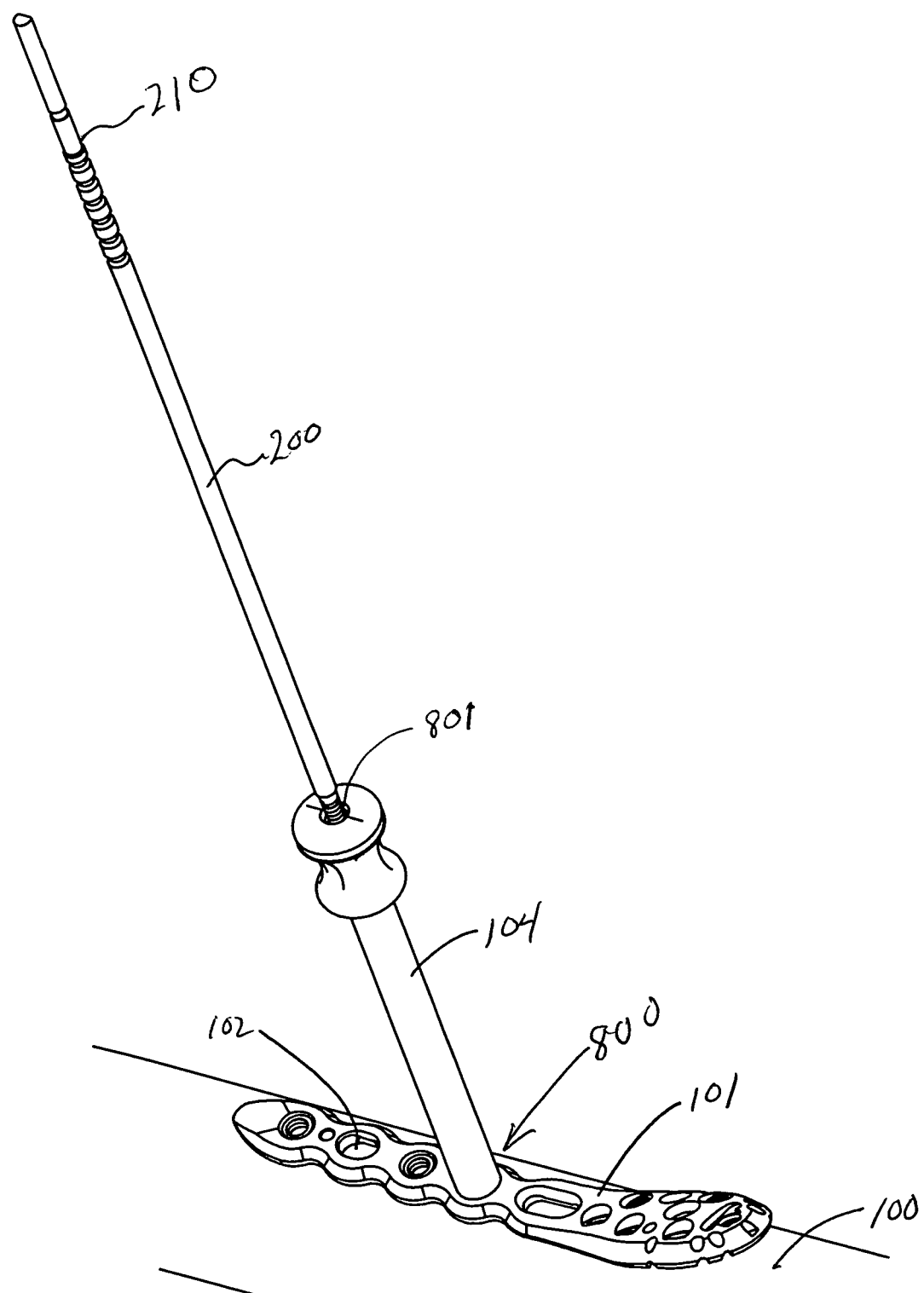

As can be taken from FIG. 8 and FIG. 9, a self-tapping and self-drilling holding pin 200 is inserted into a bone 100 through the hole 102 of the bone plate 101 using a pin sleeve 104. The outer diameter of the pin 200 thread essentially corresponds to an inner diameter of a bone screw (not shown). With this concept, it is not necessary to pre-drill again. It is possible that the inner diameter of the bone screw is the root diameter of the thread The pin sleeve inserter 104 has a tip 800 with an outer surface matching the shape of the hole 102 of bone plate 101. The inserter 104 has a bore 801 to receive and guide the threaded pin 200.

Figure 10:
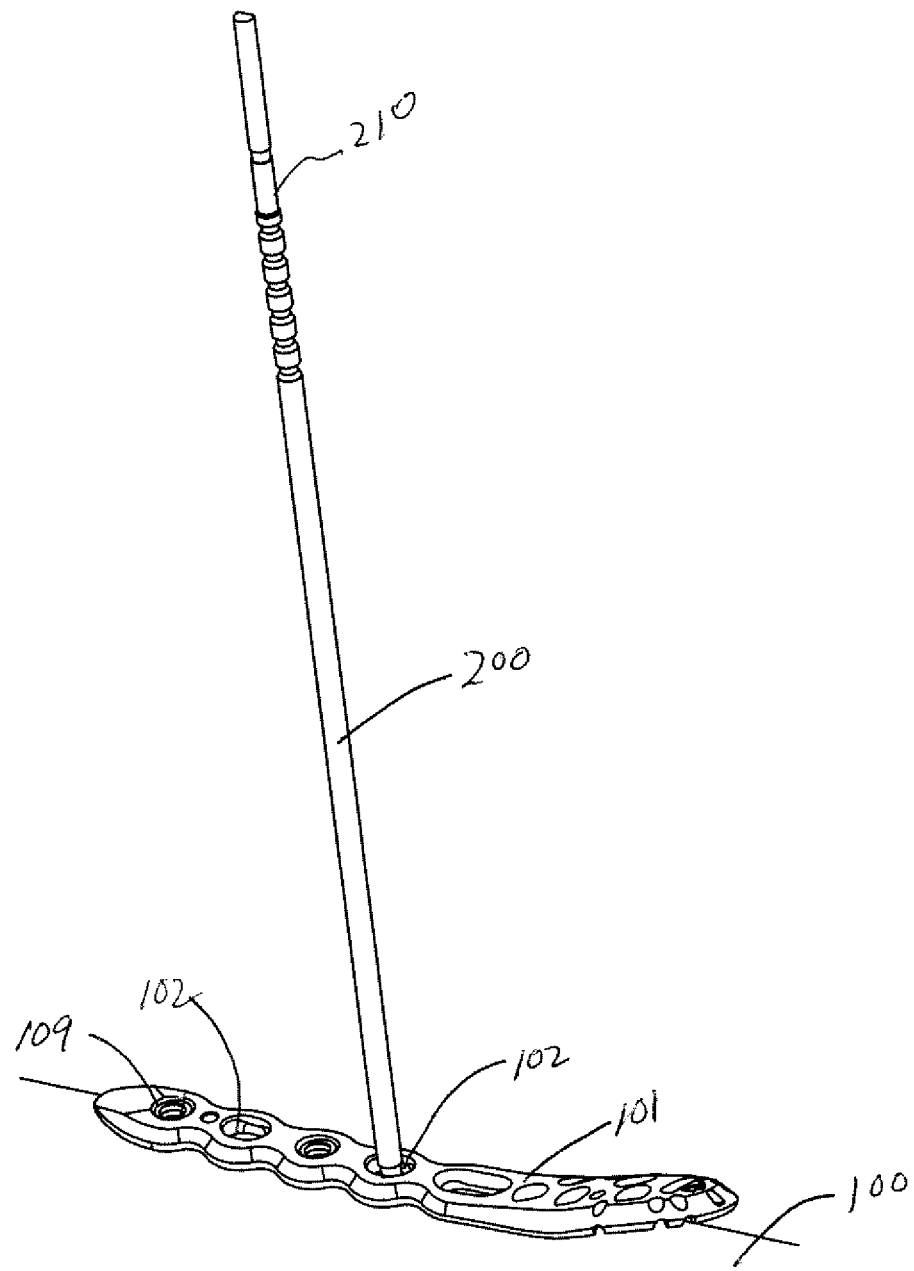

FIG. 10 shows the pin 200 in an operation state in which it is inserted into the hole 102 of the implant 101.

Figure 11:
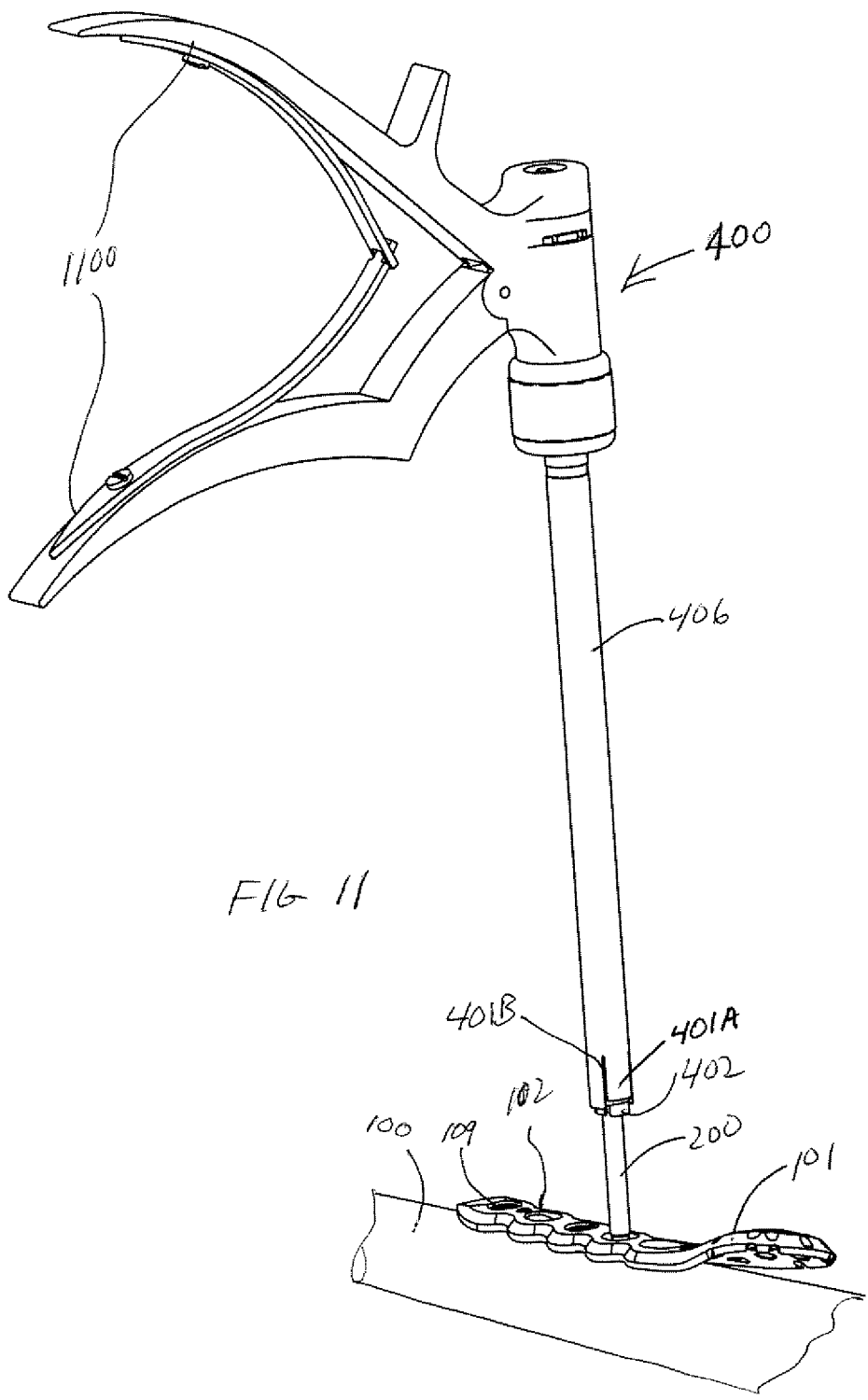

FIG. 11 shows the locking insert forceps 400 mounted on and guided by the pin 200. The locking insert forceps 400 has to be inserted till it contacts the plate 101 (while pushing a button, see grip 1100).

Figure 12:
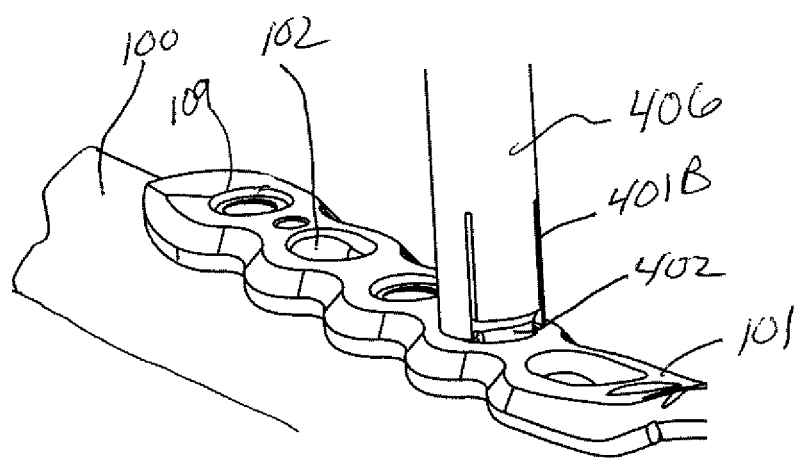

As can be taken from FIG. 12, the locking insert 402 is clamped in the hole 102 of the bone plate 101.

Figure 13:
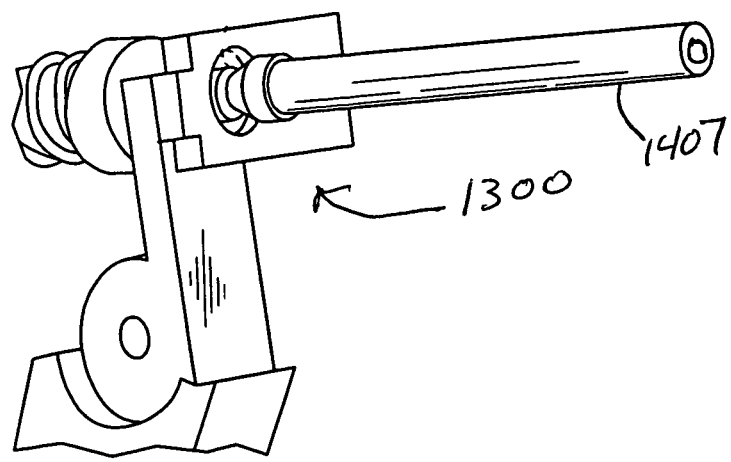
Figure 13A:
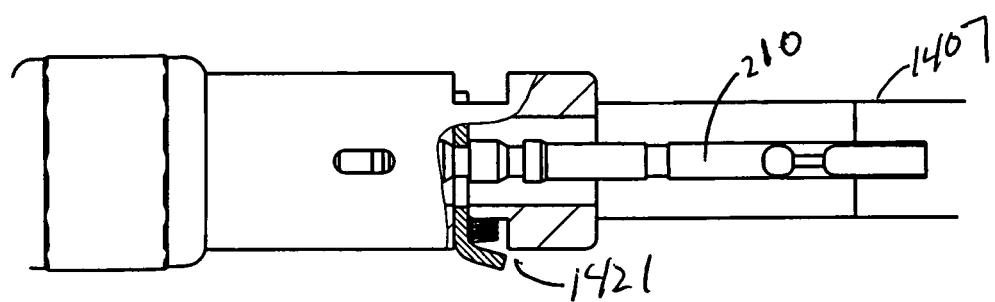

FIGS. 13 and 13A show a snap mechanism 1300 for gripping an end 210 of pin 200.

The forceps 400 is pressed so that the forceps 400 engages in a nut of the pin 200 (snap mechanism 1300). With this concept, the counterforce for inserting the insert 402 can be built up.

Figure 20:
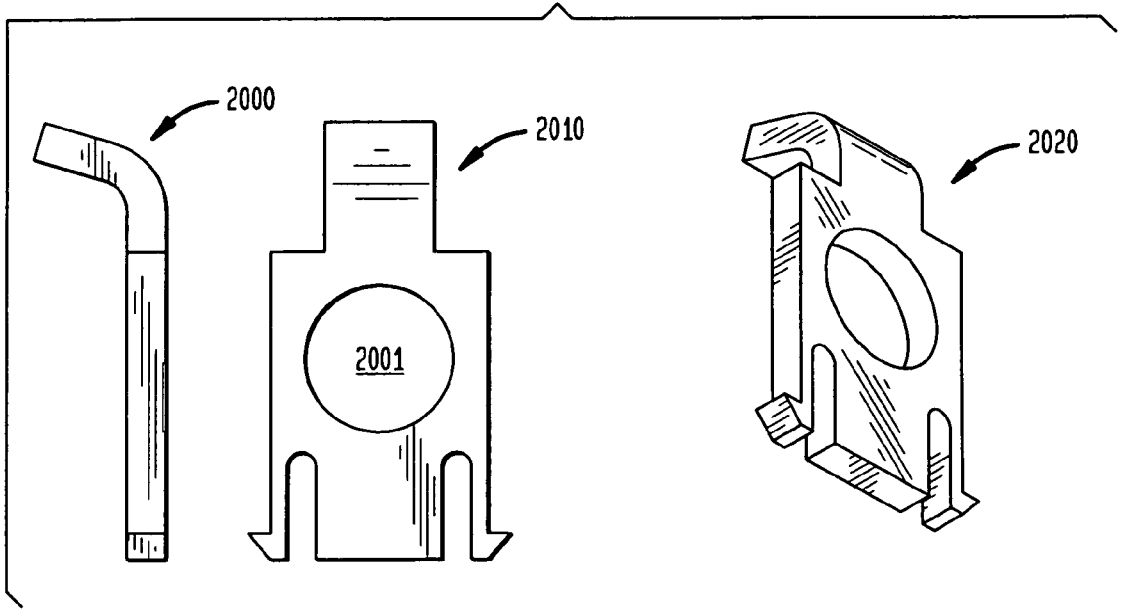
FIG. 20 illustrates a button sheet or plate of the locking insert forceps according to an exemplary embodiment of the invention.

After that, the locking insert forceps 400 may be removed by pressing the button (see FIG. 20). Then, the pin 200 can be removed.

The snap mechanism 1300 may include a spring loaded detent which may engage a groove integrally formed adjacent the end of pin 200.

In the following, referring to FIG. 14 to FIG. 20, a locking insert forceps system according to an exemplary embodiment of the invention will be explained.

Figure 14:
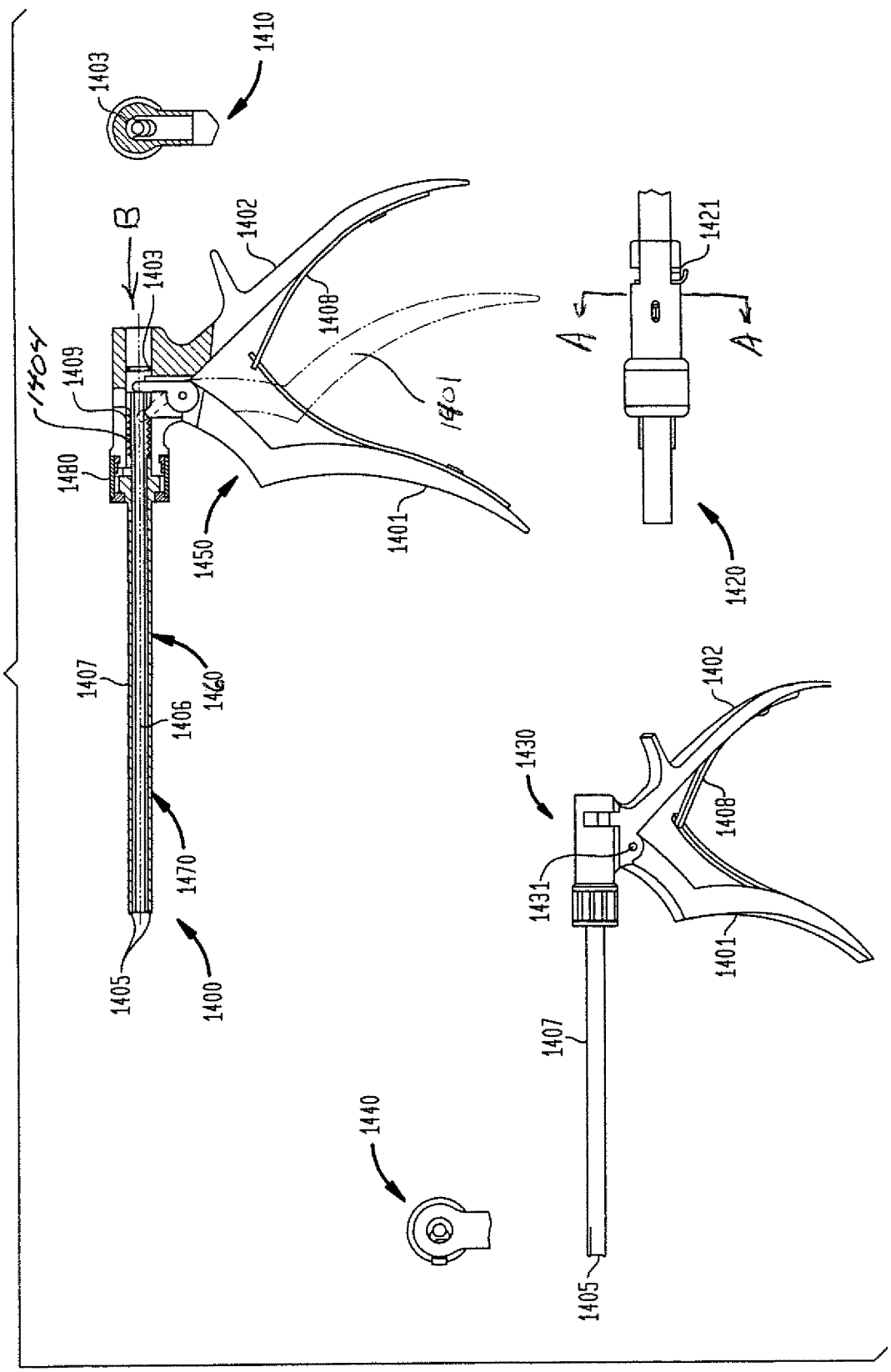
FIG. 14 illustrates different views of a locking insert forceps according to an exemplary embodiment of the invention.

FIG. 14 shows different views of a locking insert forceps.

A view 1400 shows a cross-sectional view of the locking insert forceps. An illustration 1420 shows a further cross-sectional view. A view 1410 illustrates a cross-sectional view along a line A-A. A view 1430 is a three-dimensional view of the locking insert forceps. A view 1440 is a view along a direction B.

A grip is shown comprising a first leg 1401 and a second leg 1402. Only the first leg 1401, not the second leg 1402, can be manually shifted by handling the grip 1401, 1402 as indicated by dot and dashed lines in FIG. 14. Moreover, a biasing element 1408 is illustrated. Furthermore, a button element 1403 is shown.

A spring 1404 is adapted to center the button element 1403.

A flat spring element 1405 is provided for attaching an insert element (not shown in FIG. 14).

Beyond this, a guiding channel 1406 is defined as an inside portion of an oblong tube 1407.

The button element 1403 may be operated for releasing the forceps/pin connection. A closure screw 1431 is shown which may be secured by a laser dot. A portion 1421 is secured as well by a laser dot.

The locking insert forceps of FIG. 14 is assembled based on a housing member 1450, an inner tube member 1460, a shaft member 1470, and a nut member 1480.

As hand grip 1401 is moved towards hand grip 1402, tubular guiding channel 1406 is moved within stationary tube (barrel) 1407 towards bone plate 101, thereby forcing insert 402 into bore 102 of the bone plate 101.

The mechanism of FIG. 14 is spring-centered (see spring 1421). The sliding part (button) 1403 had a bore which may engage in grooves of the pin. By the engagement, the forceps may be fixed in axial direction to prevent shifting in a direction away from the implant. When the handle 1401 is actuated in a direction towards the handle 1402, the tube 1406 moves to the front and presses the (loaded) insert element into a target component.

The nut member 1480 is not part of this mechanism but is a connecting nut by which the tube 1407 may be fixed to the grip (capable to be disassembled, for instance for cleaning purposes). For removing the forceps, the sliding part 1403 may be actuated again, thereby shifting the bore at the shifting part 1402 to such an extent that it rests coaxially to the pin. The forceps may then be removed from the pin.

Figure 15:
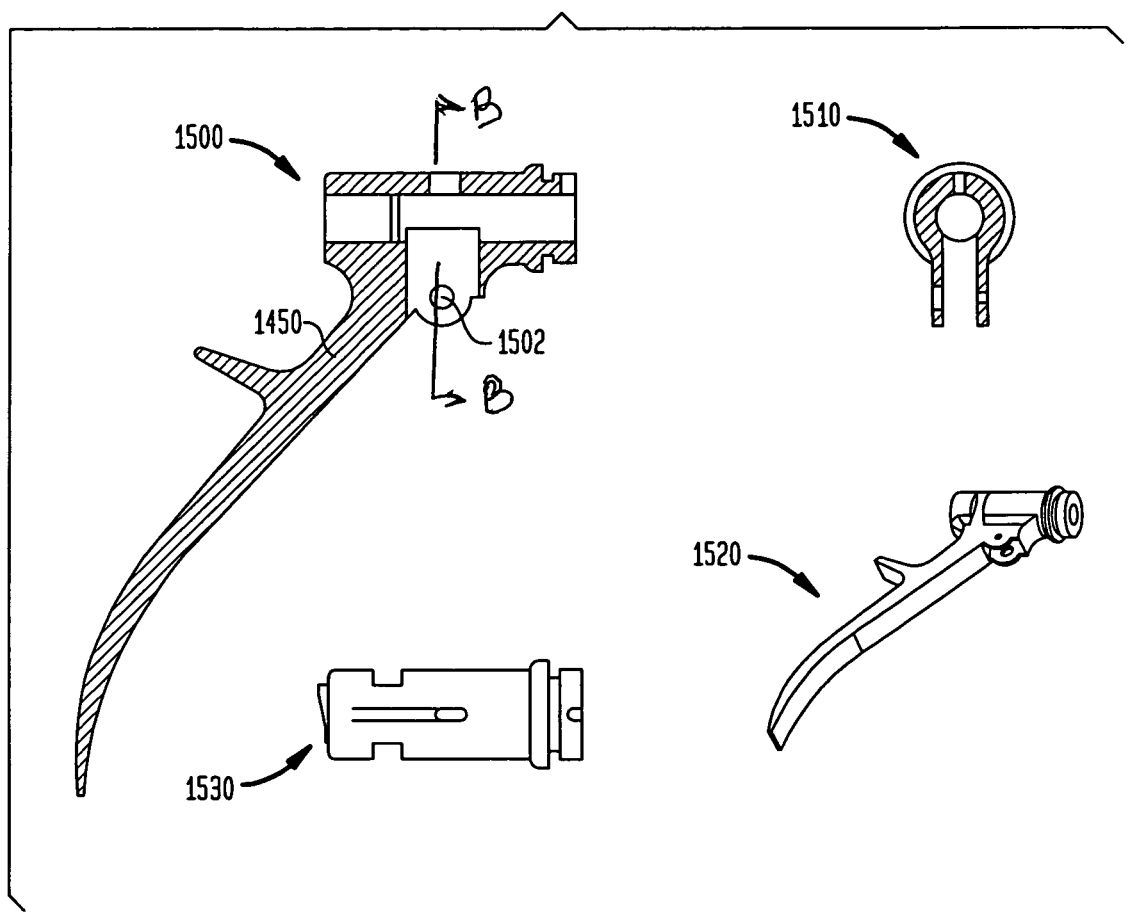
FIG. 15 illustrates different views of a housing of the locking insert forceps according to an exemplary embodiment of the invention.

FIG. 15 illustrates the housing member 1450 of the locking insert forceps of FIG. 14 in more detail.

FIG. 15 shows a plan view 1500, a cross-sectional view 1510 along a line B-B, a detailed view 1530, and a three-dimensional view 1520 of the housing 1450 of the locking insert forceps. A connection bore is indicated with reference numeral 1502.

Figure 16:
FIG. 16 illustrates an inner tube of the locking insert forceps according to an exemplary embodiment of the invention.

FIG. 16 illustrates the inner tube member 1460 of the locking insert forceps of FIG. 14 in more detail.

Figure 17:
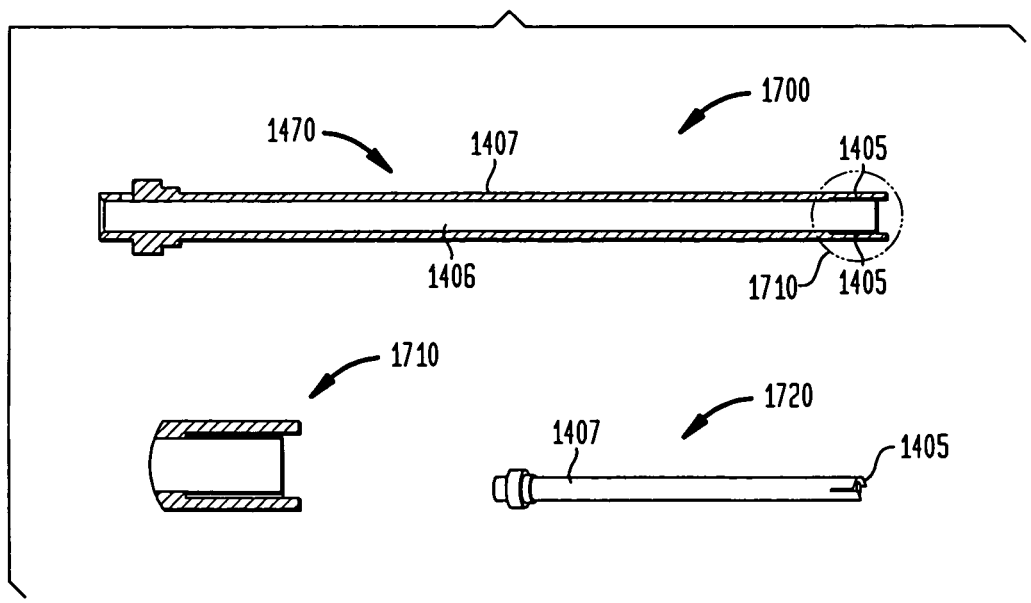
FIG. 17 illustrates different views of a shaft of the locking insert forceps according to an exemplary embodiment of the invention.

FIG. 17 illustrates the shaft member 1470 of the locking insert forceps of FIG. 14 in more detail.

FIG. 17 shows a cross-sectional view 1700, a detailed view 1710 and a three-dimensional view 1720 of a shaft 1470 of the locking insert forceps.

Figure 18:
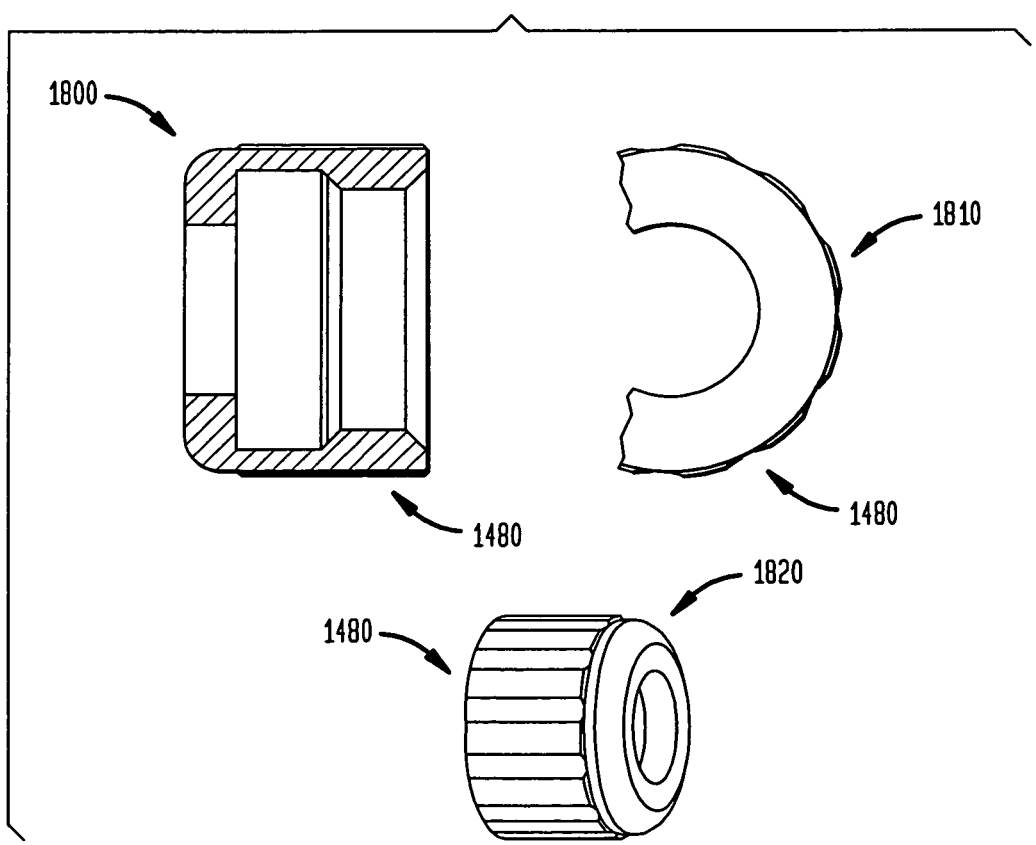
FIG. 18 illustrates different views of a connection nut of the locking insert forceps according to an exemplary embodiment of the invention.

FIG. 18 illustrates the nut member 1480 of the locking insert forceps of FIG. 14 in more detail.

FIG. 18 shows a first cross-sectional view 1800, a second cross-sectional view 1810 and a three-dimensional view 1820 of the nut 1480 of the locking insert forceps.

Figure 19:
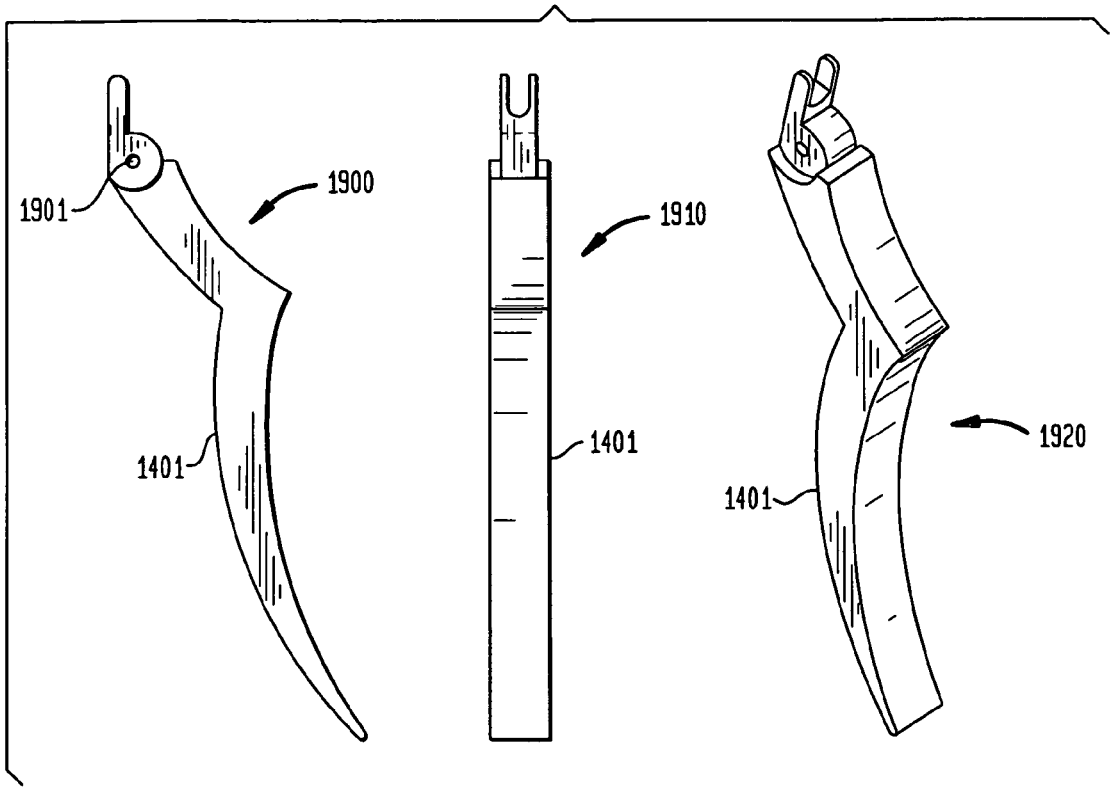
FIG. 19 illustrates different views of a front grip element of the locking insert forceps according to an exemplary embodiment of the invention.

FIG. 19 illustrates the front grip 1401 of the locking insert forceps of FIG. 14 in more detail.

FIG. 19 shows a first plan view 1900, a second plan view 1910 and a three-dimensional view 1920 of the front leg 1401 of the grip of the locking insert forceps. A connection bore 1901 is indicated in the illustration 1900.

FIG. 20 shows a first plan view 2000, a second plan view 2010 and a three-dimensional view 2020 of a button plate of the locking insert forceps.

A theoretical center is indicated with reference numeral 2001.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A medical device, the medical device comprising:
a bone implant having at least one hole therein defining an inner wall;
an insert element having an outer perimeter surface for engaging the inner wall of the hole in the bone implant, the insert having an opening therethrough inside the outer perimeter surface;
a guide pin alignable with the hole;
an insertion tool having a loading section defining an opening at least partially matching the outer surface of the insert element to be inserted into a hole formed in the bone implant wherein the insertion tool loading section resiliently holds the insert element along at least a part of the outer perimeter of the insert element;
the insertion tool having a cannulated guiding section adapted to be guided by the guide pin inserted into the hole in the bone implant for guidedly inserting the insert element into the hole in the bone implant by way of sliding the insertion tool holding the insert element along the guide pin with the guide pin received within the insert opening; and
wherein, the insertion tool further comprises a locking insert forceps mounted on the guide pin and engaging the insert element, the locking insert forceps having an actuating section for triggering insertion of the insert element into the hole formed in the implant.

2. The medical device of claim 1, wherein the insertion tool loading section comprises a spring element biased for holding the insert element.

3. The medical device of claim 2, wherein the insertion tool loading section releasably holds the insert element.

4. The medical device of claim 1, wherein the actuating section comprises at least one of the group consisting of an actuable button, an actuable switch, and an actuable grip.

5. The medical device claim 1, wherein the guiding section comprises a hollow tube through which the pin is guidable.

6. The medical device of claim 1, wherein the guiding section comprises a fastening mechanism releasably fastening the pin guided through the guiding section.

7. The medical device of claim 6, wherein the fastening mechanism is actuable by at least one of the group consisting of an actuable button, an actuable switch, and an actuable grip.

8. The medical device of claim 6, wherein the fastening mechanism is adapted to provide at least one of the group consisting of a snap-fit connection, an engagement connection, a press-fit connection, a positive locking connection, and a force closure connection.

9. The medical device of claim 1 adapted as a forceps.

10. The medical device of claim 1, adapted for inserting the insert element into the hole formed in the implant.

11. A medical kit for handling an implant, the medical kit comprising:
a medical device comprising a bone implant having at least one hole therein defining an inner wall;
a plurality of insert elements insertable into the at least one hole of the bone implant having an outer perimeter surface for engaging the inner wall of the hole in the bone implant, the insert elements having an opening therethrough inside the outer perimeter surface;
a guide pin alignable with the hole;
an insertion tool having a loading section defining an opening at least partially matching the outer surface of the insert element to be inserted into a hole formed in the bone implant wherein the insertion tool loading section resiliently holds the insert element along at least a part of the outer perimeter of the insert element;
the insertion tool having a cannulated guiding section adapted to be guided by the guide pin inserted into the hole in the bone implant for guidedly inserting the insert element into the hole in the bone implant by way of sliding the insertion tool holding the insert element along the guide pin with the guide pin received within the insert opening; and
wherein each insert element comprises a fastening element adapted to be fastened to a correspondingly designed further fastening element formed in the hole of the implant.

12. The medical kit of claim 11, wherein each insert element comprises a body having a through hole.

13. The medical kit of claim 12, wherein each insert element comprises an inner thread formed in a wall delimiting the through hole of the body.

14. The medical kit of claim 13, wherein the through hole is adapted to be penetrable by the guiding pin to be inserted into the hole formed in the implant.

15. The medical kit of claim 11, wherein the fastening element and the further fastening element are adapted to provide at least one of the group consisting of a snap-fit connection, an engagement connection, a press-fit connection, a positive locking connection, and a force closure connection.

16. The medical kit of claim 11, further comprising a plurality of implants having the hole.

17. The medical kit of claim 16, wherein the implant has a further hole, the hole being unthreaded and the further hole having an inner thread.

18. The medical kit of claim 16, wherein the implant is a bone plate.

19. The medical kit of claim 11, further comprising a pin adapted to be inserted through the hole formed in the implant into a bone.

20. The medical kit of claim 19, wherein the pin has a threaded end portion.

21. The medical kit of claim 19, wherein the pin has a self-tapping or self-drilling threaded end portion.

22. The medical kit of claim 19, wherein the pin is adapted to be guidable through the insert element and through the guiding section of the medical device.

23. The medical kit of claim 19, further comprising a pin insertion sleeve adapted to be attached to the hole formed in the implant and comprising a bore through which the pin is guidable to thereby guide the pin through the hole formed in the implant.

24. A medical device comprising:
a bone plate having at least one hole therein;
an insert having an outer perimeter for insertion into the bone plate hole, the insert having a central bore;
an insertion tool for inserting the insert into the bone plate hole comprising a cannulated body having a loading section including a spring-loaded receptacle for receiving the insert, the receptacle resiliently contacting at least part of the outer perimeter of the insert;
a guide pin aligned with the axis of the hole in the bone plate, the guide pin received in a cannulated bore of the insertion tool body and extending through the central bore in the insert, the cannulated body including an actuator means engaging the guide pin for moving the insertion tool body relative to the guide pin by sliding the insert along the guide pin; and wherein the insertion tool further comprises a locking insert forceps mounted on the guide pin and engaging the insert, the locking insert forceps having an actuating section for triggering insertion of the insert into a hole in the bone plate.

25. The medical device of claim 24, wherein the insertion tool loading section comprises a spring element formed in a wall of the receptacle biased inwardly for holding the insert.

26. The medical device of claim 24 wherein the insertion tool loading section holds the insert along at least a part of a perimeter of the insert.

27. The medical device of claim 26, wherein the insertion tool loading section releasably holds the insert.

28. The medical device of claim 24 wherein the guide pin is a bone pin having a threaded end portion.

29. The medical device of claim 28 wherein the thread is a self-drilling end.

\* \* \* \* \*